United States Patent [19]

Pelzer et al.

[11] Patent Number: 5,071,954

[45] Date of Patent: Dec. 10, 1991

[54] SYNTHETIC PROTHROMBIN PEPTIDES AND ANTIBODIES DIRECTED AGAINST THEM

[75] Inventors: Hermann Pelzer, Cölbe; Werner Stüber, Lahntal, both of Fed. Rep. of Germany

[73] Assignee: Behringwerke Aktiengesellschaft, Marburg/Lahn, Fed. Rep. of Germany

[21] Appl. No.: 234,121

[22] Filed: Aug. 17, 1988

[30] Foreign Application Priority Data

Aug. 19, 1987 [DE] Fed. Rep. of Germany ....... 3727610

[51] Int. Cl.⁵ .......................... C07K 7/06; C07K 7/08; C07K 7/10; C07K 17/02
[52] U.S. Cl. ................................... 530/324; 530/325; 530/326; 530/327; 530/328; 530/387; 530/806
[58] Field of Search ............... 530/328, 327, 326, 325, 530/324, 806, 387

[56] References Cited

PUBLICATIONS

Textbook of Immunology, James T. Barrett, pp. 72–75, 1978.
Walz, D. A., "Amino Acid Sequence of Prothrombin Fragments 1 and 2", Proc. Natl. Acad. Sci. U.S.A., vol. 74(5), pp. 1969–1972.
Lau et al., "The Isolation and Characterization of a Specific Antibody Population . . .", J. Biological Chemistry V 254 (18), Sep. 25, 1979.

*Primary Examiner*—Margaret Moskowitz
*Assistant Examiner*—Nina Ossanna
*Attorney, Agent, or Firm*—Finnegan, Henderson, Farabow, Garrett, and Dunner

[57] ABSTRACT

The invention relates to synthetic peptides which have amino acid sequences which correspond, in whole or in part, to the amino acid sequence of prothrombin and are antigenic, to the use thereof for the immunization of an animal and for the purification of specific antibodies, to antibodies against these peptides, and to the use of the antibodies for the determination of the fragments $F_2/F_{1+2}$.

5 Claims, No Drawings

SYNTHETIC PROTHROMBIN PEPTIDES AND ANTIBODIES DIRECTED AGAINST THEM

The invention relates to synthetic peptides, to the use of these peptides for immunizing an animal and for purifying specific antibodies against the said peptides, to antibodies against these peptides, and to the use of these antibodies.

The human organism has two systems, which are in equilibrium, to protect itself both from blood loss and from thromboses: the coagulation system and the fibrinolytic system. The relationship between the two systems ensures that insoluble fibrin polymers are produced initially to stop bleeding and, during wound healing, are cleaved again by the lytic progress of fibrinolysis.

Plasmin and thrombin are the key enzymes in both systems. Under physiological conditions, the dynamic equilibrium between the coagulation and the fibrinolysis system is under the control of the thrombolytic activity of plasmin and the thromboplastic activity of thrombin.

Thrombin is a typical serine protease and is synthesized in the form of an inactive precursor, prothrombin. Activation of prothrombin is based on proteolysis by coagulation factor Xa, which represents a central position within the coagulation cascade. Factor X itself has a special function in that it can be activated both by the extrinsic and by the intrinsic coagulation pathway. Activated factor X (factor Xa) activates prothrombin by specific cleavage of the prothrombin molecule at the peptide bonds following the tetrapeptide Ile-Glu-Gly-Arg. This cleavage produces, on the one hand, thrombin and, on the other hand, in equimolar concentration the prothrombin fragment $F_{1+2}$. Since one molecule of thrombin and one molecule of prothrombin fragment $F_{1+2}$ are produced from each prothrombin molecule, cleaved, determination of the prothrombin fragment $F_{1+2}$ in blood or plasma allows a direct conclusion about the coagulation potential, which depends on the thrombin concentration present in blood or plasma.

The quantification of thrombin or the prothrombin fragments $F_2/F_{1+2}$ using radioimmunoassays is known from the state of the art. The antisera required are produced by using the prothrombin fragments $F_2$ and $F_{1+2}$, obtained from purified prothrombin molecules, for immunizing animals. The specific antibodies are concentrated from the resulting crude antisera by purification by immunoadsorption on immobilized prothrombin and the corresponding fragments. These antibody preparations are suitable for the determination of the prothrombin fragments $F_2/F_{1+2}$, but do not enable a complete differentiation between intact uncleaved prothrombin and the prothrombin fragments $F_2/F_{1+2}$ liberated by cleavage. Furthermore, the relatively low specificity of this antibody preparation permits determination of the antigen only by use of radioimmunoassays (RIA) which can be carried out in practice only if the conditions set out in the radiation protection regulations are observed and, for this reason, require relatively great technical elaboration and financial cost. Finally, it is continually necessary to prepare fresh antibodies labeled with radioactive isotopes because the isotope iodine-125 normally used for the radiolabeling of proteins has a half-life of only about 2 months.

Hence the object of the present invention was to provide antigens which result in the production of specific antibodies against the prothrombin fragments $F_2/F_{1+2}$ and thus allow rapid and accurate determination of the content of these fragments in biological fluids.

This object is achieved according to the invention by synthetic peptides which have amino acid sequences which partly correspond to the amino acid sequence of prothrombin and are antigenic.

Thus the invention relates to peptides which have amino acid sequences which partly correspond to the carboxyl-terminal end of the fragments $F_2/F_{1+2}$ resulting from the FXa cleavage of thrombin, and which contain the amino acid sequence H-Gly-Asp-Glu-Glu-Gly-Val-Trp-Cys-Tyr-Val-Ala-Gly-Lys-Pro-Gly-Asp-Phe-Gly-Tyr-Cys-Asp-Leu-Asn-Tyr-Cys-Glu-Glu-Ala-Val-Gln-Glu-Glu-Thr-Gly-Asp-Gly-Leu-Asp-Glu-Asp-Ser-Asp-Glu-Glu-Arg-Ala-Ile-Glu-Gly-Arg-OH, in whole or in part, but at least the four carboxyl-terminal amino acids.

Suitable for the preparation of the peptides according to the invention are conventional methods, for example Merrifield solid-phase peptide synthesis (G. Barany and R. B. Merrifield: "Solid-Phase Peptide Synthesis" in E. Gross and J. Meienhofer: The Peptides, Analysis, Synthesis, Biology, Academic Press, Inc. 1980) as well as customary synthetic strategies constructing the peptides in the form of soluble peptide segments. The peptide of the structure H-Cys(SH)-Leu-Asp-Glu-Asp-Ser-Asp-Glu-Glu-Arg-Ala-Ile-Glu-Gly-Arg was particularly preferably prepared on the solid phase. The Fmoc group has been used as temporary protective group, and the permanent protective groups used were the O-t-Bu protective group for Asp and Glu, t-Bu for Ser, the Mtr group for Arg and the tert.-butylmercapto group for Cys. The C-terminal amino acids were immobilized via p-alkoxybenzyl ester groups which were bonded to 1% crosslinked polystyrene. The peptides were constructed with repeated elimination of the temporary protective group and condensation of the next, protected amino acid using a condensing agent, preferably a carbodiimide. The peptides were cleaved off the resin by acidolysis with simultaneous deprotection of the side-chain groups. Any sulfhydryl groups to be deprotected are deprotected using tri-n-butylphosphine according to the state of the art. The peptides were purified by ion exchange chromatography, RP-HPLC and gel permeation chromatography. The composition of the peptides was confirmed as correct by amino acid analysis.

The use of synthetic peptides as antigens in the immunization of animals results in the generation of antibodies specifically directed against the hapten exposed in this peptide. Hence the antibodies generated in this way are each specific for a single antibody-binding site of the complete protein from which the peptide sequence has been derived. Compared with the use of the natural, purified prothrombin fragments $F_2/F_{1+2}$, the use of synthetic peptides has two additional profound advantages; synthetic peptides can be prepared on a large scale and in high purity so that the elaborate isolation and purification of the natural prothrombin fragments is avoided. Whereas the purification of synthetic peptides from by-products of the synthesis is well established, even technically elaborate enrichment and purification processes for natural prothrombin fragments always result in preparations which contain a proportion of undesired peptides which, although not detectable still has antigenic activity.

The peptide prepared according to the invention has an amino acid sequence which corresponds completely or in part to the amino acid sequence of prothrombin and is synthesized by one of the conventional processes for peptide synthesis, for example Merrifield synthesis. The selection of the appropriate sequence entails, where possible, selection of the regions which, due to their location on the protein and/or the antigenicity of the exposed epitope, can be predicted to have a highly antigenic effect. The synthetic peptide then has antigenic activity, so that an immune response is triggered by immunization.

Activated factor X (Xa) cleaves the prothrombin molecule at the recognition sequence Ile-Glu-Gly-Arg. Hitherto this tetrapeptide has been detected only in human and bovine prothrombin. The rarity of this tetrapeptide predisposes it for use as a specific feature of the prothrombin molecule.

Prothrombin is cleaved by activated factor X next to the arginine of the sequence Ile-Glu-Gly-Arg. Thus, factor Xa generates a new carboxyl terminus which contains in the terminal region the two amino acids Glu and Arg which have a very high antigenicity index. Peptides or polypeptides which contain the recognition sequence of the factor Xa cleavage site at the C terminus are particularly well suited for immunization.

It has emerged, surprisingly, that antibodies directed against a peptide or polypeptide which contains at its C-terminal end the sequence of the tetrapeptide of the recognition sequence for the factor Xa protease react specifically and exclusively with the prothrombin fragment which has been cleaved off and not with the intact prothrombin molecule.

The fragment produced by the action of factor Xa on prothrombin and which has the factor Xa recognition sequence at the C terminus has a chain length of 273 amino acids. Suitable for immunization are both the entire polypeptide as well as part-sequences of this peptide which, however, still need to have the factor Xa recognition sequence at the C terminus. A particularly preferred embodiment provides for the use of a tetradecapeptide, for example having the sequence Leu-Asp-Glu-Asp-Ser-Asp-Glu-Glu-Arg-Ala-Ile-Glu-Gly-Arg-OH. The only important point in each case is that the carboxylterminal sequence of the molecule is exposed and results in the immunization.

Shorter peptides suffice in cases where it is not intended for the peptide to trigger an immune response but it is intended that the only function of this peptide is to be recognized by existing antibodies. An embodiment appropriate for this is based on an octapeptide of the sequence Glu-Glu-Arg-Ala-Ile-Glu-Gly-Arg-OH.

In view of the intended use of the peptides, it is appropriate to introduce amino acids with reactive side groups into the peptides in such a way that they do not affect the structure of the hapten. For this reason, it is expedient to attach to the N terminus cysteine as a further amino acid, the free SH group of which is suitable for coupling via thioethers to many carriers. An example which is preferably provided is the antigen represented by the abovementioned peptide in the form of the pentadecapeptide Cys(SH)-Leu-Asp-Glu-Asp-Ser-Asp-Glu-Glu-Arg-Ala-Ile-Glu-Gly-Arg.

The peptide used for the immunization can be prepared both by customary means by chemical synthesis and by purification of a polypeptide made available by genetic manipulation. A conceivable example would be genetic engineering synthesis of the prothrombin fragment $F_2$ or $F_{1+2}$ in *E. coli* controlled by a strong promoter, or else the synthesis, by genetic manipulation, of a peptide extending beyond the factor Xa cleavage site or a peptide which is subsequently cleaved in vitro by factor Xa, which is likewise obtained by genetic engineering, which results in accessibility to the desired antigenic carboxyl terminus.

It is worthwhile for peptides which are intended to be used for immunization, or those intended to be employed as an immunoadsorbent, to be coupled to a carrier molecule. Examples of customary carrier molecules which are widely used are bovine serum albumin, ovalbumin and polysaccharides. In a preferred embodiment, the peptide or polypeptide is bound to keyhole limpet hemocyanin.

When the synthetic peptides according to the invention are used as immunoadsorbents, it is advisable to couple to materials suitable for preparing solid matrices. A preferred embodiment provides for the coupling of short peptides, for example the abovementioned octapeptide, to Sepharose which has been activated with cyanogen bromide.

Immunization of suitable animals with carrier-bound peptides results reproducibly in the production of antibodies. A preferred animal species for immunization and obtaining antibodies in this context is the rabbit, because in this case there is a favorable relationship between the blood volume obtainable and the expense of breeding and care.

The immunoglobulin fraction relevant for specific assays can be enriched by customary immunoadsorption methods from an antiserum of this type generated in an animal using synthetic peptides according to the invention. However, it is preferred in this case likewise to use as material for a matrix of this type, which is employed for immunoadsorption, a peptide which is coupled to a carrier and has the same antigenic determinant as the peptide employed for the immunization. The peptide used for the purification by immunoadsorption can moreover be considerably shorter; the only prerequisite for use in purification of the desired antibody by immunoadsorptionis that the antigenic determinant formed by this shorter polypeptide is recognized and efficiently bound by the desired antibody.

The peptide used for purification of the antibodies by immunoadsorption can be, for example, an octapeptide, preferably the peptide H-Glu-Glu-Arg-Ala-Ile-Glu-Gly-Arg.

According to the invention, antibodies are induced in the animal system by immunization with synthetic peptides and are purified by immunoadsorption. These antibodies react specifically with the peptides used for the immunization and purification. Depending on the sequence of the peptide used, these antibodies bind either only to the fragments $F_2$ and $F_{1+2}$ or else, if a peptide sequence which is exposed in the natural prothrombin molecule is chosen, to the intact prothrombin molecule.

It is possible, by choosing appropriate peptides as immunoadsorbents, to select antibodies which react specifically with the antigenic determinant of prothrombin which corresponds to the sequence of the factor Xa cleavage site of this molecule; in the preferred case where peptides which have the factor Xa-recognition sequence at the C terminus are used both for the immunization and for the purification by immunoadsorption there is enrichment of antibodies against this sequence, but these do not react with intact natural prothrombin, because the factor Xa cleavage site in the natural prothrombin molecule either is not sufficiently exposed or does not have the higher structure required for recognition as an antigen.

The antibodies obtained according to the invention can be employed for a number of immunoassays with a variety of designs. For this purpose, they are expediently coupled to a solid carrier, but are preferably immobilized by adsorption onto polystyrene tubes. The tubes prepared for the following immunoassays can then be stored, closed airtight, at 4° C.

The amount of prothrombin fragments $F_2/F_{1+2}$ is determined according to the invention by preincubation of the sample with immobilized antibodies of this type, with the concentration of the fragments $F_2/F_{1+2}$ which are bound by the immobilized antibodies being detected by subsequent incubation with a second antibody. This second antibody must have a property which is measurable, for example the ability to react with or bind a chromogenic substrate.

It is expedient for this second antibody to be coupled to a marker enzyme, preferably peroxidase. However, it is also possible to choose to provide the second antibody either with a fluorescent molecule, for example fluorescein isothiocyanate or else with a radioactive label.

The prothrombin fragments $F_2/F_{1+2}$ can also be determined by simultaneous incubation of the sample, preferably of plasma, and labeled antibodies with the immobilized antibodies. Also possible is a competitive determination method entailing competition of labeled and unlabeled prothrombin fragments $F_2/F_{1+2}$ for the binding site on the immobilized antibodies.

The concentration of prothrombin fragments $F_2/F_{1+2}$ determined in this way provides information on the degree of activation of the prothrombin.

The examples illustrate the invention. The following abbreviations are used in the examples:
FPA: fibrinopeptide A
ELISA: enzyme immunoassay (enzyme-linked immunosorbent assay)
RIA: radioimmunoassay
KLH: keyhole limpet hemocyanin
PBS: phosphate-buffered saline
Tris: tris(hydroxymethyl)aminomethane
EDTA: ethylenedinitrilotetraacetic acid
OD: absorbance (optical density)
Asp: L-aspartic acid
Ala: L-alanine
Arg: L-arginine
Gly: glycine
Glu: L-glutamic acid
Ile: L-isoleucine
Ser: L-serine
Cys(SH): L-cysteine
Fmoc: 9-fluorenylmethyloxycarbonyl
O-t-Bu: tert.-butyl ester
t-Bu: tert.-butyl ether
Mtr: 4-methoxy-2,3,6-trimethylphenylsulfonyl
DMF: dimethylformamide
RP-HPLC: reversed phase high performance liquid chromatography
GMBS: gamma-maleimidobutyric acid hydroxysuccinimide ester

EXAMPLE 1

Preparation of an Antigen for the Immunization a) Peptide synthesis for the pentadecapeptide H-Cys(SH)-Leu-Asp-Glu-Asp-Ser-Asp-Glu-Glu-Arg-Ala-Ile-Glu-Gly-Arg The peptide was synthesized using a semiautomatic peptide synthesizer. 1 g of Fmoc-Arg (Mtr)-p-alkoxybenzyl ester-resin was deprotected with 15 ml of 20% piperidine/DMF (v/v) and then washed several times with DMF and isopropanol. 1 mmol of Fmoc-Gly (3-fold excess) and 203 mg of HOBt dissolved in 15 ml of DMF were added. 1.1 ml of a 1M diisopropylcarbodiimide solution (dichloromethane) were added and then the coupling was carried out for 1.5 hours. Excess reagents were removed by washing with DMF and isopropanol. This coupling scheme was maintained up to the N-terminal amino acid. The last amino acid employed was a Boc-protected amino acid. Every coupling step was checked for completeness by a ninhydrin test. 1.06 g of resin were stirred with 2.5 ml of thioanisole, 2.5 ml of ethanedithiol and 15 ml of trifluoroacetic acid at 35° C. for 4 hours and were filtered off. The acidic solution was poured into ether, and the precipitated peptide was filtered off and chromatographed on a Sephadex ® G 25 column (3×100 cm, 0.5% acetic acid). The peptide pool was lyophilized. Yield: 230 mg of peptide.

b) Deprotection of the sulfhydryl group 70 mg of the peptide were dissolved in 7 ml of trifluoroethanol and 350 µl of water, and the pH was adjusted to 7.3 with N-methylmorpholine. The reaction vessel was flushed with nitrogen, and 40 µl of n-tributylphosphine were added. The mixture was stirred at room temperature for 1 hour and was diluted with 50 ml of water, and the pH was adjusted to 4.0. The aqueous phase was extracted three times with 10 ml of diethyl ether, concentrated to 10 ml and purified on Sephadex ® G 25 (3×100 cm; 0.5% acetic acid). Yield: 55 mg of peptide.

c) Preparation of conjugate 30 mg of keyhole limpet hemocyanin were dissolved in 0.05 mM sodium phosphate buffer, pH 8.0, and were activated with 3 mg of GMBS for 1 hour. The protein was chromatographed on a Sephadex ® G 50 column (2×30 cm) (0.1M sodium phosphate; 0.5 mM EDTA, pH 6.0). The protein pool was concentrated to 6 ml and incubated with 30 mg of the peptide containing sulfhydryl groups for 1 hour. Yield after dialysis and lyophilization: 38 mg of peptide conjugate.

EXAMPLE 2

Immunization of Rabbits 5 rabbits were immunized with 2 mg of antigen per animal each time for a period of 8 weeks; the peptide-KLH conjugate administrations were given subcutaneously and intravenously. The animals were then exsanguinated, and the resulting crude antisera were pooled and stabilized with preservative. Yield: 850 ml of antiserum.

EXAMPLE 3

Preparation of Immunoadsorbents

For the purification of the crude antisera by affinity chromatography, about 20 mg of the octapeptide with the sequence H-Glu-Glu-Arg-Ala-Ile-Glu-Gly-Arg-OH (prepared as in Example 1a) were covalently immobilized on a solid phase. The coupling reaction was carried out with Sepharose activated with cyanogen bromide by a described method (Axen, R. et al., Nature, 214, 1302, 1967). The immunoadsorbent was then in each case washed with phosphate-buffered saline (PBS; 0.15 mol/l, pH 7.2) and acetic acid (0.5 mol/l, pH 2.5). Before use, the adsorbent was equilibrated with 3 times the gel volume of PBS. Yield: about 20 ml of peptide-Sepharose.

The tetradecapeptide prepared as in Example 1 was used in the same way to prepare an immunoadsorbent.

EXAMPLE 4

Isolation of Specific Antibodies 100 ml of crude antiserum were applied to the octapeptide-Sepharose (1.5×15 cm) equilibrated with PBS, and subsequently washed with PBS until the absorbance at 280 nm was 0.01. This was followed by washing steps with saline (1 mol/l, pH 7.0) and water (pH 7.0), with 3 times the gel volume being used in each case. The antibodies were eluted from the immunoadsorbent with 0.1 mol/l acetic acid (pH 2.5), and the antibody solution was adjusted to pH 7.0 with solid sodium phosphate (0.01 mol/l), concentrated (Amicon membrane) and stored at −70° C. Yield: 35 to 40 mg of antibody.

EXAMPLE 5

Assays of the Antibodies Obtained by Immunoadsorption a) Preparation of antibody-coated tubes The antibodies obtained in Example 4 were diluted with tris buffer solution (0.025 mol/l, pH 7.6) to a concentration of 5 µg/ml and immobilized by adsorption onto polystyrene tubes. 250 µl of antibody solution were incubated in each tube at 20° C. for 20 hours, and then the liquid was removed by aspiration, and the tubes were sealed airtight and stored at 4° C.

b) Procedure for the enzyme immunoassay (ELISA)

The samples to be assayed (plasma, serum) were diluted 1:1 with incubation buffer (0.01 mol/l tris, 0.01 mol/l EDTA, heparin (2 U/ml), 0.05% Tween, pH 7.6), and 200 µl samples in each tube (see Example 5a) were incubated at 37° C. for 30 min. The incubation solution was then removed, and the tube was washed twice with 500 µl of washing solution each time (0.02 mol/l sodium phosphate, 0.05% Tween, pH 7.6). Then 200 µl of peroxidase-conjugated anti-prothrombin antibodies were added, and the tubes were incubated at 37° C. for 30 min. After removal of the conjugate solution and two washes, 200 µl of substrate/chromagen solution (hydrogen peroxide; o-phenylenediamine) were added, and the tubes were incubated at room temperature. After incubation for ½ an hour, the peroxidase was inactivated with sulfuric acid, and the absorbance of the reaction solution at 492 nm was determined.

The absorbances at 492 nm as a function of the plasma or serum dilution are shown in the table which follows, comparing with the absorbance of a tube without plasma or serum.

TABLE 1

| Dilution | $OD_{492}/30$ min |
|---|---|
| Plasma | |
| 1:10 | 0.13 |
| 1:100 | 0.12 |
| 1:1000 | 0.11 |
| 1:10000 | 0.11 |
| Serum | |
| 1:10 | 3.72 |
| 1:100 | 3.71 |
| 1:1000 | 2,81 |
| 1:10000 | 0.97 |
| Buffer blank | 0.045 | c) Procedure for an enzyme immunoassay (ELISA) for determining fragments $F_2/F_{1+2}$ formed in vitro.

Another experiment was carried out to examine the specificity of the antibodies against the fragments $F_2/F_{1+2}$. Plasma anticoagulated with citrate solution was recalcified with calcium chloride solution (final concentration of calcium chloride: 0.025 mol/l). Aliquots were removed at various times, and the reaction was stopped by addition of EDTA (0.1 mol/l), antithrombin III (3 IU/ml) and heparin (5 IU/ml). The samples were diluted 1:1 with incubation buffer and assayed using the ELISA.

The table shows the results.

TABLE 2

| Time (min) | $OD_{492}/39$ min. |
|---|---|
| 0 | 0,18 |
| 3 | 0,30 |
| 6 | 0,32 |
| 12 | 0.58 |
| 15 | 1,20 |
| 18 | 1,69 |
| 21 | 1,88 |
| 25 | 1,96 |
| Buffer blank | 0,045 |

The results show that the fragments $F_2/F_{1+2}$ can be measured quantitatively in this way: the concentration of the fragments $F_2/F_{1+2}$ increases with increasing time during the recalcification reaction.

The peptides according to the invention, which have an amino acid sequence which corresponds, in whole or in part, to the amino acid sequence of prothrombin and is antigenic thus induce binding-specific antibodies against each of the antigenic determinants present in the peptide. These specific antibodies can then be purified by immunoadsorption on peptides having the same antigenic determinants. The use of synthetic peptides has the considerable advantage that absolutely pure antigens are employed for the immunization, so that no cross-reaction whatever with other proteins or other parts of the prothrombin molecule can occur in the resulting immune serum. Preferably used according to the invention is a peptide which contains the factor Xa cleavage site. Using an antibody against this peptide it is possible to detect only cleaved prothrombin molecules, because this sequence is not accessible to antibody recognition in intact natural prothrombin. Measurement of the quantity of bound antibody provides direct information on the concentration of liberated prothrombin fragments $F_2/F_{1+2}$ and thus on the degree of activation of prothrombin.

We claim:

1. Peptides which have amino acid sequences which partly correspond to the carboxyl-terminal end of the fragments $F_2/F_{1+2}$ resulting from the $F X_a$ cleavage of prothrombin, and which consists essentially of all or at least eight of the carboxyl-terminal amino acids of the sequence H-Gly-Asp-Glu-Glu-Gly-Val-Trp-Cys-Tyr-Val-Ala-Gly-Lys-Pro-Gly-Asp-Phe-Gly-Tyr-Cys-Asp-Leu-Asn-Tyr-Cys-Glu-Glu-Ala-Val-Gln-Glu-Glu-Thr-Gly-Asp-Gly-Leu-Asp-Glu-Asp-Ser-Asp-Glu-Glu-Arg-Ala-Ile-Glu-Gly-Arg-OH.

2. A peptide as claimed in claim 1, which consists essentially of the amino acid sequence H-Leu-Asp-Glu-Asp-Ser-Asp-Glu-Glu-Arg-Ala-Ile-Glu-Gly-Arg-OH, H-Glu-Glu-Arg-Ala-Ile-Glu-Gly-Arg-OH or H-Cys(SH)-Leu-Asp-Glu-Asp-Ser-Asp-Glu-Glu-Arg-Ala-Ile-Glu-Gly-Arg.

3. Peptides as claimed in claim 1, which are prepared by genetic manipulation or by chemical synthesis.

4. A peptide as claimed in claim 1, which is bound to an insoluble polymeric carrier, keyhole limpet hemocyanin, albumin or ovalbumin.

5. Antibodies which bind to peptides as claimed in any one of claims 1 to 4, which have been obtained by immunization of an animal with said peptides and subsequent purification by immunoadsorption.

* * * * *

UNITED STATES PATENT AND TRADEMARK OFFICE
CERTIFICATE OF CORRECTION

PATENT NO. : 5,071,954

DATED : December 10, 1991

INVENTOR(S) : Hermann Pelzer et al.

It is certified that error appears in the above-identified patent and that said Letters Patent is hereby corrected as shown below:

Claim 1, column 9, line 3, delete "F $X_a$" and insert therefor --F Xa--.

Signed and Sealed this

Thirtieth Day of November, 1993

Attest:

BRUCE LEHMAN

*Attesting Officer*  *Commissioner of Patents and Trademarks*